US00PP33618P2

(12) United States Plant Patent
Jones

(10) Patent No.: US PP33,618 P2
(45) Date of Patent: Nov. 2, 2021

(54) ***AGASTACHE* PLANT NAMED 'ASURO08-0'**

(50) Latin Name: ***Agastache* hybrid**
Varietal Denomination: ASURO08

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 17/093,907

(22) Filed: Nov. 10, 2020

(51) Int. Cl.
*A01H 5/02* (2018.01)
*A01H 6/50* (2018.01)

(52) U.S. Cl.
USPC ..... Plt./399

(58) Field of Classification Search
USPC ..... Plt./399
CPC ... A01H 5/02; A01H 5/00; A01H 6/50; A01H 6/00; A01H 6/1424
See application file for complete search history.

(56) References Cited

PUBLICATIONS

Germania Seed Green Leaf Plants Perennial Starter Plants Program #01 2019, retrieved on Mar. 1, 2020, retrieved from the Internet at https://germaniaseed.com/pdf/2020/701_greenleaf.pdf, pp. 1 and 19. (Year: 2019).*

Skagit Horticulture 2020-21 Liner Catalog, retrieved on Mar. 1, 2020, retrieved from the Internet at https://www.skagithort.com/liners/wp-content/uploads/sites/3/2020/10/2020-21-Liner-Catalog-FINAL-medium.pdf, pp. 1-4, 12, 107-111. (Year: 2020).*

* cited by examiner

*Primary Examiner* — June Hwu
(74) *Attorney, Agent, or Firm* — Cassandra Bright

(57) ABSTRACT

A new and distinct cultivar of *Agastache* plant named 'ASURO08-0' is disclosed, characterized by unique rose flowers, and increased branching. Plants are vigorous and produce densely flowering verticillasters. The new cultivar is an *Agastache*, suitable for ornamental garden purposes.

2 Drawing Sheets

Latin name of the genus and species: *Agastache* hybrid.
Variety denomination: 'ASURO08-0'.

BACKGROUND OF THE INVENTION

The new cultivar is the result of a planned breeding program by the inventor. An open-pollination of multiple unnamed, unpatented, proprietary varieties of *Agastache* was made in August 2018 in Santa Paula, Calif. Seed was bulk collected and planted for out in trial conditions. 'ASURO08-0' was found and selected in April 2019 in the group of plants resulting from the above open-pollination.

The first asexual propagation of 'ASURO08-0' occurred in April 2019 by terminal vegetative cuttings at a nursery in Santa Paula, Calif. Subsequent propagation has shown that the unique features of this cultivar are stable and reproduced true to type in several successive generations.

SUMMARY OF THE INVENTION

The following are the unique combination of characteristics of this new cultivar when grown under standard horticultural practices in Santa Paula, Calif.:

1. Unique rose-colored flowers.
2. Increased branching.
3. Densely flowering verticillaster.
4. Vigorous plants.

COMPARISON TO PARENT VARIETIES

The exact parentage of 'ASURO08-0' cannot be determined as an open-pollination involving multiple parents was made and seed bulk collected.

COMMERCIAL COMPARISON

'ASURO08-0' can be compared to the commercial variety *Agastache* 'Acapulco Rose', unpatented. Plants of the two cultivars are similar in most horticultural characteristics. Plants of the new cultivar 'ASURO08-0', however, differ in the following:

1. The new variety produces more branches than this comparator.
2. The new variety produces more inflorescences than this comparator.
3. Flowers of the new variety are stacked more tightly on the verticillaster than flowers of this comparator.
4. The new variety is overall more floriferous than this comparator, having more inflorescences, and denser inflorescences with more flowers.

'ASURO08-0' can be compared to the commercial variety *Agastache* 'ASUBL01-0', U.S. Plant Pat. No. 32,376. Plants of the two cultivars are similar in most horticultural characteristics. Plants of the new cultivar 'ASURO08-0', however, differ in the following:

1. The new variety produces rose-colored flowers; this comparator produces violet colored flowers.

BRIEF DESCRIPTION OF THE PHOTOGRAPHS

'ASURO08-0' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Agastache*.

DETAILED BOTANICAL DESCRIPTION

Figure 1:
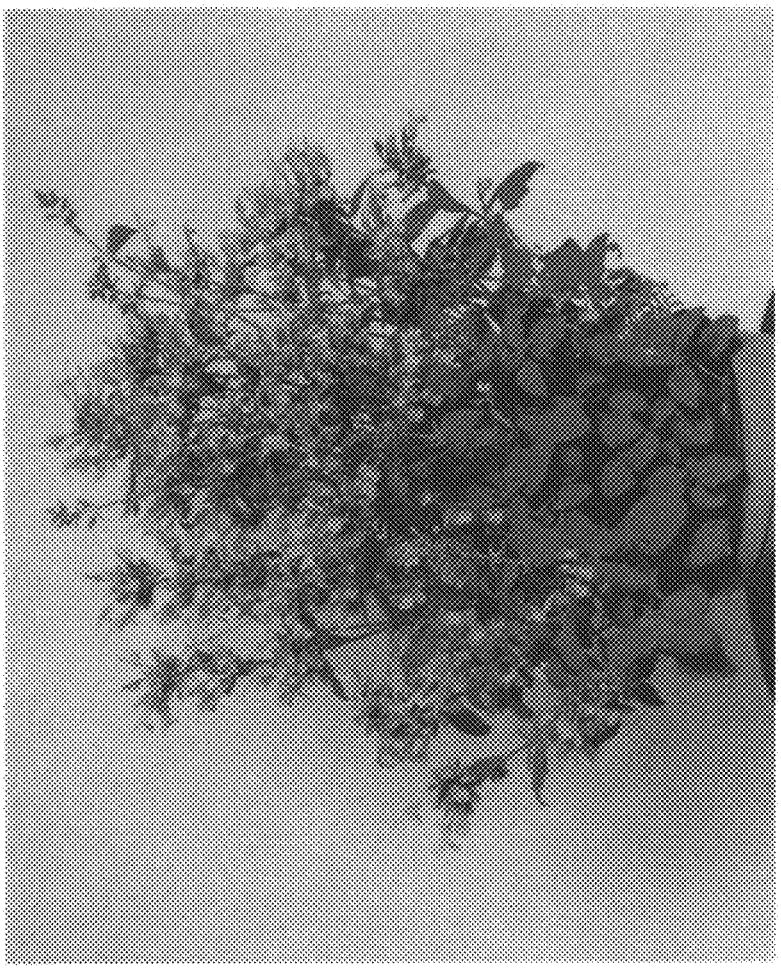
FIG. 1 shows a plant of the new variety at about 6 months old from a rooted cutting grown in a greenhouse in Santa Paula, Calif. during Spring.
Figure 2:
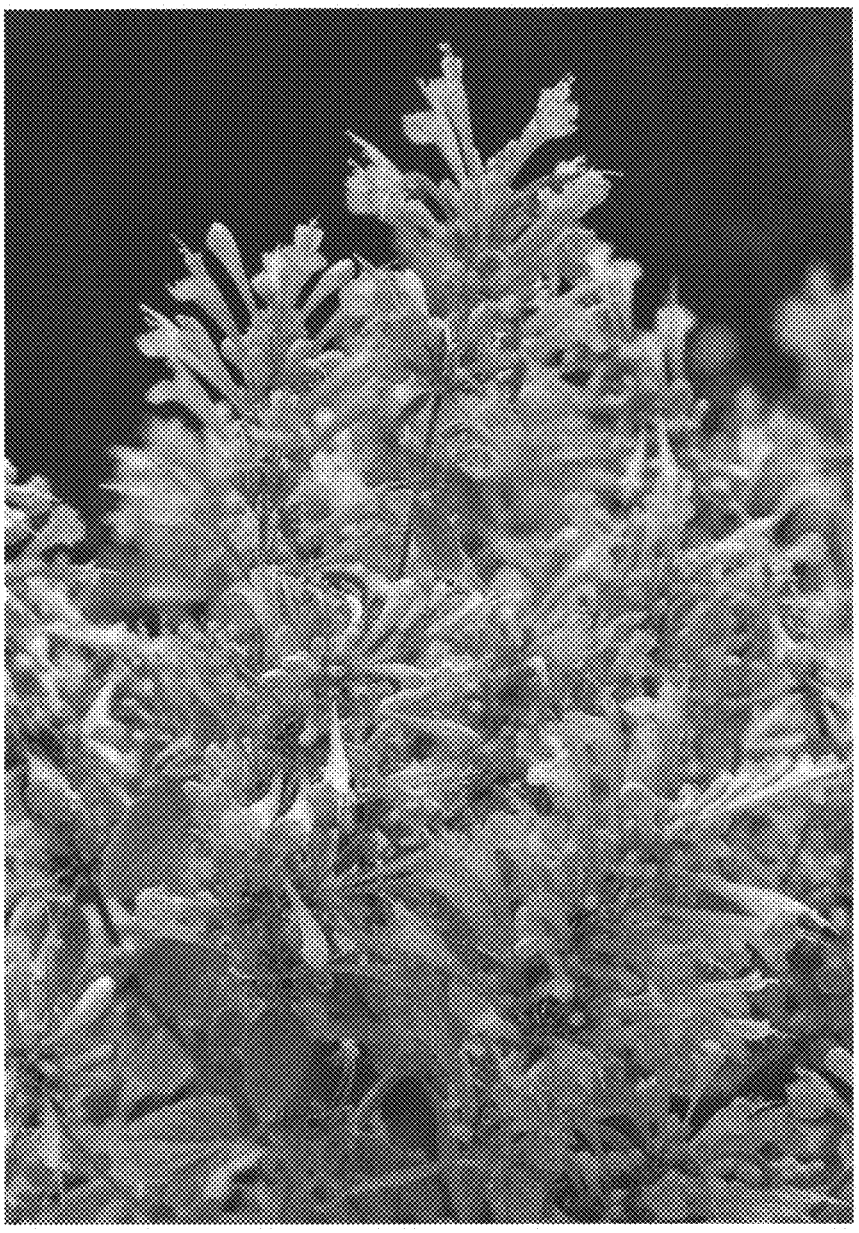
FIG. 2 shows a close-up view of the inflorescence.

The following is a detailed description of the botanical characteristics of the new and distinct hybrid *Agastache* known by the denomination 'ASURO08-0'. The detailed description was taken of an 8 month old plant in Santa Paula, Calif. All colors cited herein refer to The Royal Horticultural Society Colour Chart (R.H.S.), 2007 Edition.

Botanical classification: *Agastache* 'ASURO08-0'.

PROPAGATION

Time to initiate roots: About 20 days at approximately 20 to 22° C.

Root description: Fine, densely fibrous.

Time to produce a rooted cutting: About 21 days at 22° C.

PLANT

Growth habit: Upright to outwardly arching perennial. Annual in climates with low temperatures below 0° C.

Pot size of plant described: 8 inch.

Height: Approximately 32 cm to top of flowering plane, approximately 22 cm to top of foliage plane.

Plant spread: Approximately 30 cm.

Growth rate: Rapid.

Branching characteristics: Free-branching.

Length of primary lateral branches: Approximately 6 to 9 cm, foliage section only.

Diameter of lateral branches: Approximately 0.3 cm.

Quantity of lateral branches: Approximately 4 to 8 branches emerge from a pinch.

Stem:

*Color*.—Near RHS Green N138A.

*Pubescence*.—Very short, dense pubescence.

*Other stem characteristics*.—Quadrangular.

Internode length: Averages between 2.2 to 3.2 cm.

Age of plant described: Approximately 20 weeks from 3 rooted cuttings.

FOLIAGE

Leaf:

*Arrangement*.—Opposite.

*Quantity*.—Approximately 10 to 12 fully expanded leaves per main branch.

*Average length*.—Approximately 5.5 cm.

*Average width*.—Approximately 2.9 cm.

*Shape of blade*.—Deltoid.

*Apex*.—Acute.

*Base*.—Truncate.

*Attachment*.—Stalked.

*Margin*.—Infrequently serrate.

*Texture of top surface*.—Velvety.

*Texture of bottom surface*.—Glabrous.

*Color*.—Young foliage upper side: Near RHS Green 137A. Young foliage under side: Near RHS Green 138A. Mature foliage upper side: Near RHS Green 141B. Mature foliage under side: Near RHS Green 141C.

*Venation*.—Type: Pinnate. Venation color upper side: Near RHS Yellow-Green 144B. Venation color under side: Near RHS Green 138B.

*Petiole*.—Average Length: Approximately 1.3 cm. Diameter: Approximately 0.1 cm. Color: Near RHS Green 141C.

*Foliage fragrance*.—Very strong aromatic, somewhat minty scent.

FLOWER

Natural flowering season: Flowering begins early Spring and continues through late Summer.

Inflorescence type and habit: Flowers arranged in verticillasters. Individual flowers self-cleaning, calyx persistent.

Flower longevity on plant: Individual flowers approximately 8 days on the plant without significant color loss or other degradation.

Quantity and arrangement of flowers: Between 16 and 24 fully opened flowers per blooming spike, at one time; about 50 blooming spikes per plant. About 10 to 18 flowers per whorl, including flower buds. Average 5 to 7 whorls per inflorescence. Whorls are densely arranged towards top of inflorescences, bottom 2 or 3 whorls interrupted (about 2 to 3.5 cm between whorls).

Inflorescence size:

*Diameter*.—Approximately 7.0 cm.

*Height*.—Average range 6 to 12.0 cm.

Peduncle:

*Length*.—Average range 2.8 to 4.1 cm.

*Diameter*.—3 mm.

*Color*.—Near RHS Green 139C.

*Orientation*.—Straight.

*Texture*.—Pubescent and ridged.

*Strength*.—Strong.

Pedicel:

*Length*.—Average range 2.0 to 3.0 mm.

*Diameter*.—1 mm.

*Color*.—Near RHS Green 139D.

*Orientation*.—Straight.

*Texture*.—Pubescent.

*Strength*.—Soft and flexible.

Corolla:

*Petal arrangement*.—The corolla is highly fused, zygomorphic, bilabiate. 1 upper lip with 2 lobes, and 2 smaller lateral petals with single lobes and 2 slightly larger highly fused lobes forming a lower lip.

*Margin*.—Entire.

*Petal apex shape*.—Obtuse.

*Entire corolla length*.—Approximately 3.2 cm.

*Entire corolla width*.—Approximately 0.7 cm.

*Attachment aspect*.—About 45° to stem.

*Persistence*.—Non-persistent.

*Fragrance*.—Very aromatic, strong somewhat minty scent.

Petal:

*Length*.—Upper lip Approximately 0.4 cm, lower lip Approximately 0.5 cm. Laterals Approximately 0.3 cm.

*Width*.—Upper lip Approximately 0.5 cm, lower lip approximately 0.6 cm, laterals Approximately 0.3 cm.

*Texture*.—Glabrous.

*Tube*.—Length: About 2.2 cm. Width: About 0.4 cm at widest point.

Color:

*Petals*.—When opening: Interior surface: Near RHS Red 38A. Exterior surface: Near RHS Red 48B flushed Orange-Red 35A. Fully opened: Interior surface: Near RHS Red-Purple 73C, upper section 73D. Exterior surface: Near RHS Red-Purple N74D. Fading: Interior surface: Near RHS Red-Purple 73D. Exterior surface: Near RHS Red-Purple 73C.

Floral tube:

*When opening*.—Interior surface: Near RHS Red-Purple 73C heavily flushed Red 40D. Exterior surface: Near RHS Red-Purple N74D heavily flushed Red 40D.

*Fully opened*.—Interior surface: Near RHS Red-Purple 70D. Exterior surface: Near RHS Red-Purple N74D.

*Fading*.—Interior surface: Near RHS Red-Purple 69B. Exterior surface: Near RHS Red-Purple 73D.

Bud:

*Shape*.—Curved ovoid.

*Length*.—Approximately 1.4 cm.

*Diameter*.—Approximately 0.4 cm.

*Color*.—Near RHS Orange-Red 32B; apex Red 40C.

Calyx:

*Length*.—Approximately 0.6 cm.

*Diameter*.—Approximately 0.3 cm.

*Shape*.—Tubular.

Sepals:

*Shape*.—5 sepals fused to form a tube.

*Apex*.—Highly acute.

*Margin*.—Entire.

*Texture*.—Pubescent. Ridged.

*Color*.—Near RHS Green 138C flushed Violet 86D.

*Persistence*.—Persistent.

REPRODUCTIVE ORGANS

Stamens:

*Number*.—4.

*Filament length*.—Approximately 1.3 cm lower 50% fused to petals.

*Filament color*.—Near RHS Red-Purple 70C.

Anthers:

*Shape*.—Elliptic.

*Length*.—Approximately 1 mm.

*Color*.—Near RHS Red-Purple 70A.

*Pollen*.—Moderate.

*Pollen color*.—Near RHS Red-Purple 70D.

Pistil:

*Number*.—1.

*Length*.—Approximately 2.1 cm, not fused to floral parts.

*Style*.—Length: Approximately 1.9 cm. Color: Near RHS Red-Purple 73C.

*Stigma*.—Shape: Two-parted cleft. Color: Near RHS Red-Purple 73D. Ovary color: Near RHS Red-Purple 69D.

OTHER CHARACTERISTICS

Disease and pest resistance: Not observed to be susceptible nor resistant to normal diseases and pests of *Agastache*.

Temperature tolerance: The new variety tolerates temperatures between 0 to 40° C.

Fruit/seed production: Not observed.

What is claimed is:

1. A new and distinct cultivar of *Agastache* plant named 'ASURO08-0' as herein illustrated and described.

* * * * *